US008133866B2

(12) United States Patent
Stern et al.

(10) Patent No.: US 8,133,866 B2
(45) Date of Patent: Mar. 13, 2012

(54) METHOD FOR INHIBITING NEW TISSUE GROWTH IN BLOOD VESSELS IN A PATIENT SUBJECTED TO BLOOD VESSEL INJURY

(75) Inventors: David M. Stern, Great Neck, NY (US); Ann Marie Schmidt, Franklin Lakes, NJ (US); Steven Marso, Shawnee, KS (US); Eric Topol, Chagrin Falls, OH (US); A. Michael Lincoff, Orange Village, OH (US)

(73) Assignees: The Trustees of Columbia University in the City of New York, New York, NY (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 12/802,485

(22) Filed: Jun. 7, 2010

(65) Prior Publication Data

US 2010/0292134 A1 Nov. 18, 2010

Related U.S. Application Data

(63) Continuation of application No. 11/894,809, filed on Aug. 20, 2007, now Pat. No. 7,732,400, which is a continuation of application No. 09/687,528, filed on Oct. 13, 2000, now abandoned.

(51) Int. Cl.
  *C07K 19/00* (2006.01)
  *C07K 14/00* (2006.01)
  *A61K 39/395* (2006.01)
  *A01N 25/00* (2006.01)

(52) U.S. Cl. ............... 514/16.5; 514/9.4; 424/134.1; 530/350

(58) Field of Classification Search .................. None
See application file for complete search history.

(56) References Cited

U.S. PATENT DOCUMENTS

| 5,698,531 | A | 12/1997 | Nabel et al. |
| 5,833,651 | A | 11/1998 | Donovan et al. |
| 5,843,102 | A | 12/1998 | Kalmann et al. |
| 5,864,018 | A | 1/1999 | Morser et al. |
| 5,879,380 | A | 3/1999 | Kalmann et al. |
| 6,071,514 | A | 6/2000 | Grinnell et al. |
| 6,465,422 | B1 | 10/2002 | Schmidt et al. |
| 6,555,340 | B1 | 4/2003 | Schmidt et al. |
| 6,555,651 | B2 | 4/2003 | Stern et al. |
| 6,563,015 | B1 | 5/2003 | Stern et al. |
| 6,670,136 | B2 | 12/2003 | Schmidt et al. |
| 6,677,299 | B2 | 1/2004 | Stern et al. |
| 6,753,150 | B2 | 6/2004 | Schmidt et al. |
| 6,790,443 | B2 | 9/2004 | Stern et al. |
| 6,825,164 | B1 | 11/2004 | Stern et al. |
| 7,026,444 | B2 | 4/2006 | Schmidt et al. |
| 7,081,241 | B1 | 7/2006 | Schmidt et al. |
| 7,101,838 | B2 | 9/2006 | Stern et al. |
| 7,125,675 | B2 | 10/2006 | Schmidt et al. |
| 7,258,857 | B2 | 8/2007 | Stern et al. |
| 2004/0228855 | A1 | 11/2004 | Stern et al. |
| 2005/0129682 | A1 | 6/2005 | Schmidt et al. |
| 2006/0078562 | A1 | 4/2006 | Mjalli et al. |
| 2006/0140933 | A1* | 6/2006 | Pittman et al. ............. 424/133.1 |
| 2007/0099829 | A1 | 5/2007 | Stern et al. |
| 2008/0019986 | A1 | 1/2008 | Stern et al. |
| 2008/0207499 | A1 | 8/2008 | Barile et al. |

FOREIGN PATENT DOCUMENTS

| WO | WO 97/00857 | 7/1997 |
| WO | WO 97/39121 | 10/1997 |
| WO | WO 97/39125 | 10/1997 |
| WO | WO 98/22138 | 5/1998 |
| WO | WO 99/18987 | 4/1999 |

OTHER PUBLICATIONS

Rozenman, Y., et al., (1997) "Long-Term Angiographic Follow-Up of Coronary Balloon-Angioplasty in Patients With Diabetes Mellitus: A Clue to the Explanation of the Results of the BARI Study (Balloon Angioplasty Revascularization Investigation)." *J. Am. Coll. Cardiol.* 30:1420-1425.

Detre, KM., et al. (2000) "For the BARI Investigators. The Effect of Previous Coronary Artery Bypass Surgery on the Prognosis of Patients With Diabetes Who Have Acute Myocardial Infarction." *N. Engl. J. Med.* 342:989-997.

K., et al. (1999) "Diabetes and the Decline in Heart Disease Mortality in United States Adults." *JAMA* 281:1291-1297.

Schmidt AM, et al.(1992) "Isolation and Characterization of Two Binding Proteins for Advanced Glycosylation End Products From Bovine Lung Tissue Which Are Present on the Endothelial Cell Surface." *J. Biol. Chem.* 267:14987-14997.

Neeper, M et al. (1992) "Cloning and Expression of RAGE: A Cell Surface Receptor for Advanced Glycation End Products of Proteins." *J. Biol. Chem.* 267:14998-15004.

Lander, HM. et al., (1997) "Activation of the Receptor for Advanced Glycation Endproducts Triggers A P21ras-Dependent MAP Kinase Pathway Regulated by Oxidant Stress." *J. Biol. Chem.*, 272:17810-17814.

(Continued)

*Primary Examiner* — Elly-Gerald Stoica
(74) *Attorney, Agent, or Firm* — John P. White; Cooper & Dunham LLP

(57) ABSTRACT

This invention provides for a method for inhibiting new tissue growth in blood vessels in a subject, wherein the subject experienced blood vessel injury, which comprises administering to the subject a pharmaceutically effective amount of an inhibitor of receptor for advanced glycation endproduct (RAGE) so as to inhibit new tissue growth in the subject's blood vessels. The invention also provides for method for inhibiting neointimal formation in blood vessels in a subject, wherein the subject experienced blood vessel injury, which comprises administering to the subject a pharmaceutically effective amount of an inhibitor of receptor for advanced glycation endproduct (RAGE) so as to inhibit neointimal formation in the subject's blood vessels. The invention also provides a method for preventing exaggerated restenosis in a diabetic subject which comprises administering to the subject a pharmaceutically effective amount of an inhibitor of receptor for advanced glycation endproduct (RAGE) so as to prevent exaggerated restenosis in the subject.

8 Claims, 2 Drawing Sheets

OTHER PUBLICATIONS

Hofman, MA., et al. (1999) "RAGE Mediates a Novel Proinflammatory Axis: A Central Cell Surface Receptor for S100/Calgranulin Polypeptides." *Cell* 97:889-901.

Park, L. et al. (1998) "Suppression of Accelerated Diabetic Atherosclerosis by Soluble Receptor for AGE (sRAGE)." *Nature Medicine*, 4:1025-1031.

Schmidt, AM., et al. (1994) "Receptor for Advanced Glycation Endproducts (Ages) Has a Central Role in Vessel Wall Interactions and Gene Activation in Response to Circulating Age Proteins." *PNAS* (USA) 91:8807-8811.

Yan, SD., et al. (2000) "Receptor-Dependent Cell Stress and Amyloid Accumulation in Systemic Amyloidosis." *Nat Med.* 6:643-51.

Carter et al. (2000) "The Effects of Uncontrolled Hyperglycemia on Thrombosis and Formation of Neointima After Coronary Stent Placement in a Novel Diabetic Porcine Model of Restenosis." *Coronary Artery Disease*, 11(6):473-479.

Touchard, et al. (2006) "Preclinical Restenosis Models: Challenges and Successes." *Toxicology Pathology*, 34;11-18.

Taguchi et al., (2000) "Blockade of RAGE-Amphoterin Signaling Suppresses Tumour Growth and Metastases" *Nature*, 405-354-360.

Rudinger, (1976) "Characteristics of the Amino Acids As Components of a Peptide Hormone Sequence." *Peptide Hormones*: 1-7.

Kaye, et al. "A Single Amino Acid Substitution Results in a Retinoblastoma Protein Defective in Phosphorylation and Oncoprotein Binding" 1990, Proc. Natl. Acad. Sci., vol. 87: 6922-6926.

Skolnick, et al."From Genes to Protein Structure and Function: Novel Applications of Computational Approaches in the Genomic Era." 2000, TIBTECH, vol. 18: 34-39.

Gura, T. Science, vol. 278, p. 1041-1042, 1997.

Muller et al. (1992) *J. Amer. Coll. Cardiol.* 19(2):418-432.

Reilly et al. (1993) *Drug Dev. Res.* 29(2):137-147.

Lafont et al. (1998) *Card. Res.* 39(1):50-59.

Park, SH., et al. (2001) "Neointimal Hyperplasia After Arterial Injury Is Increased in a Rat Model of Non-Insulin-Dependent Diabetes Mellitus." *Circulation* 104:815-819.

Tomasinsig, et al. 2005, Current Protein and Peptide Science, vol. 6, p. 23-24.

Renard, et al. (1999) "The Human and Rat Recombination Receptors for Advanced Glycation Endproducts Have a High Degree of Homology But Different Pharmacokinetic Properties in Rats." *J. Pharmacology and Experimental Therapeutics*, 250(3):1458-1466.

Naka et al. (2004) *Arteriosclerosis, Thrombosis and Vascular Biology.* 24:1342-1349.

Stern et al., U.S. Appl. No. 08/592,070, filed Jan. 26, 1996, including the pending claims.

PCT International Application No. PCT/US97/21197 published May 28, 1998, Publication No. WO/98/22138.

PCT International Application No. PCT/US98/21346 published Apr. 22, 1999, Publication No. WO/99/18987.

Allowed claims for U.S. Appl. No. 11/319,949, filed Dec. 27, 2005.

Pending claims for U.S. Appl. No. 09/498,459, a 371 national stage entry of PCT/US98/16303 filed Aug. 5, 1998.

Schmidt et al., U.S. Appl. No. 11/891,680, filed Aug. 9, 2007, including the pending claims.

Pending claims for U.S. Appl. No. 11/584,310, filed Oct. 20, 2006.

Pending claims for U.S. Appl. No. 11/807,884, filed May 29, 2007.

Pending claims for U.S. Appl. No. 11/805,164, filed May 21, 2007.

Stern et al., U.S. Appl. No. 12/009,572, filed Jan. 18, 2008, including the pending claims.

U.S. Appl. No. 09/638,648, filed Aug. 14, 2000, including the pending claims.

U.S. Appl. No. 10/840,927, filed May 7, 2004, including the pending claims.

Pending claims for U.S. Appl. No. 10/990,310, filed Nov. 15, 2004.

Pending claims for U.S. Appl. No. 11/801,635, filed May 9, 2007.

Pending claims for U.S. Appl. No. 11/894,503, filed Aug. 20, 2007.

Marie Schmidt et al., U.S. Appl. No. 10/570,674, a 371 national stage of PCT International Application No. PCT/US04/28712, filed Sep. 3, 2004, including pending claims.

Shi Du Yan et al., U.S. Appl. No. 10/577,506, a 371 national stage of PCT International Application No. PCT/US04/36170, filed Oct. 28, 2004, including pending claims.

Shi Du Yan et al., U.S. Appl. No. 10/577,382, a 371 national stage of PCT International Application No. PCT/US04/36173, filed Oct. 28, 2004, including the pending claims.

Pending claims for U.S. Appl. No. 11/477,274, filed Jun. 28, 2006.

Pending claims for U.S. Appl. No. 11/197,644, filed Aug. 3, 2005.

Pending claims for U.S. Appl. No. 11/630,916, a 371 national stage of PCT International Application No. PCT/US05/27694, filed Aug. 3, 2005.

Pending claims for U.S. Appl. No. 10/850,861, filed May 20, 2004.

* cited by examiner

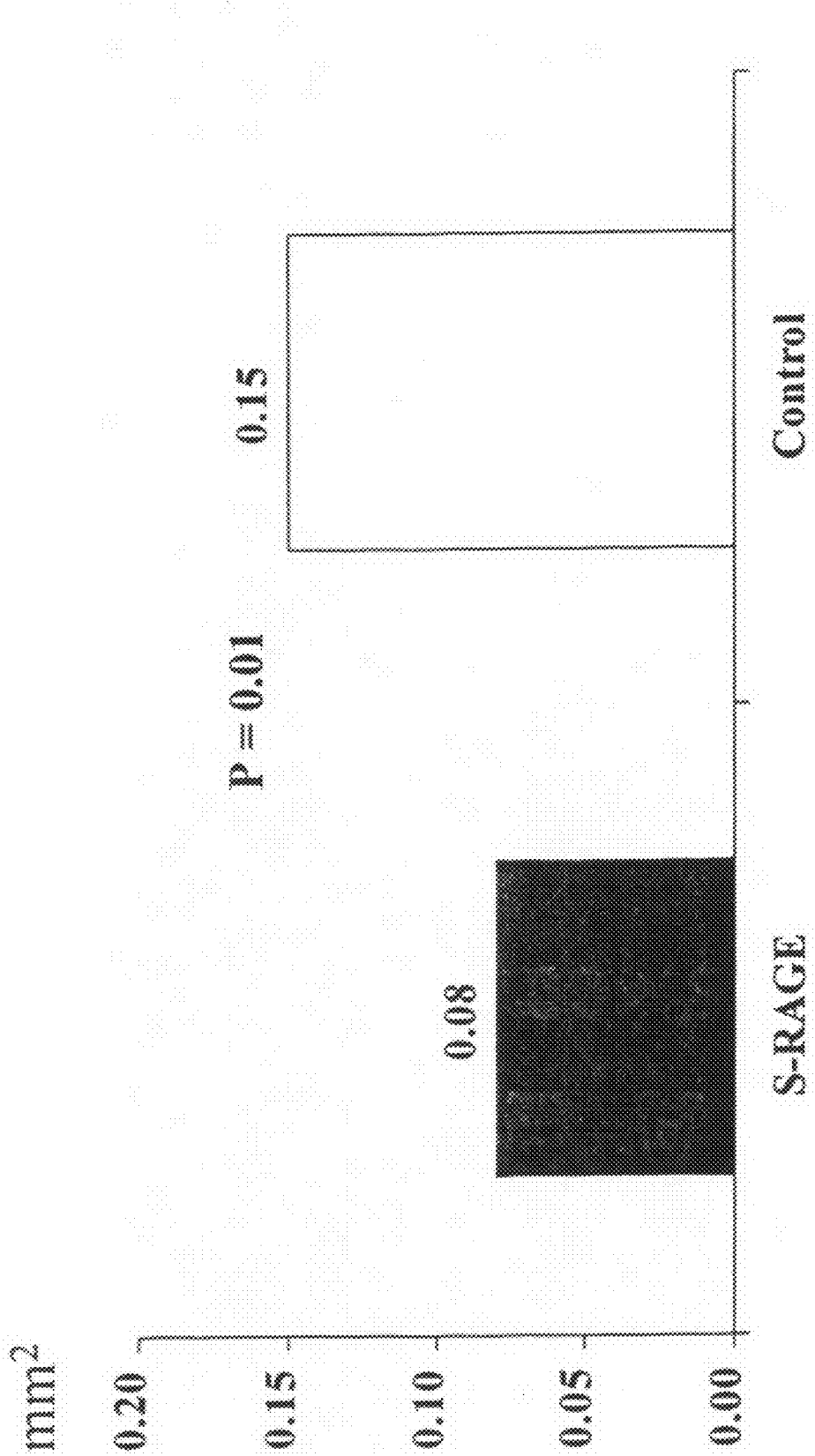

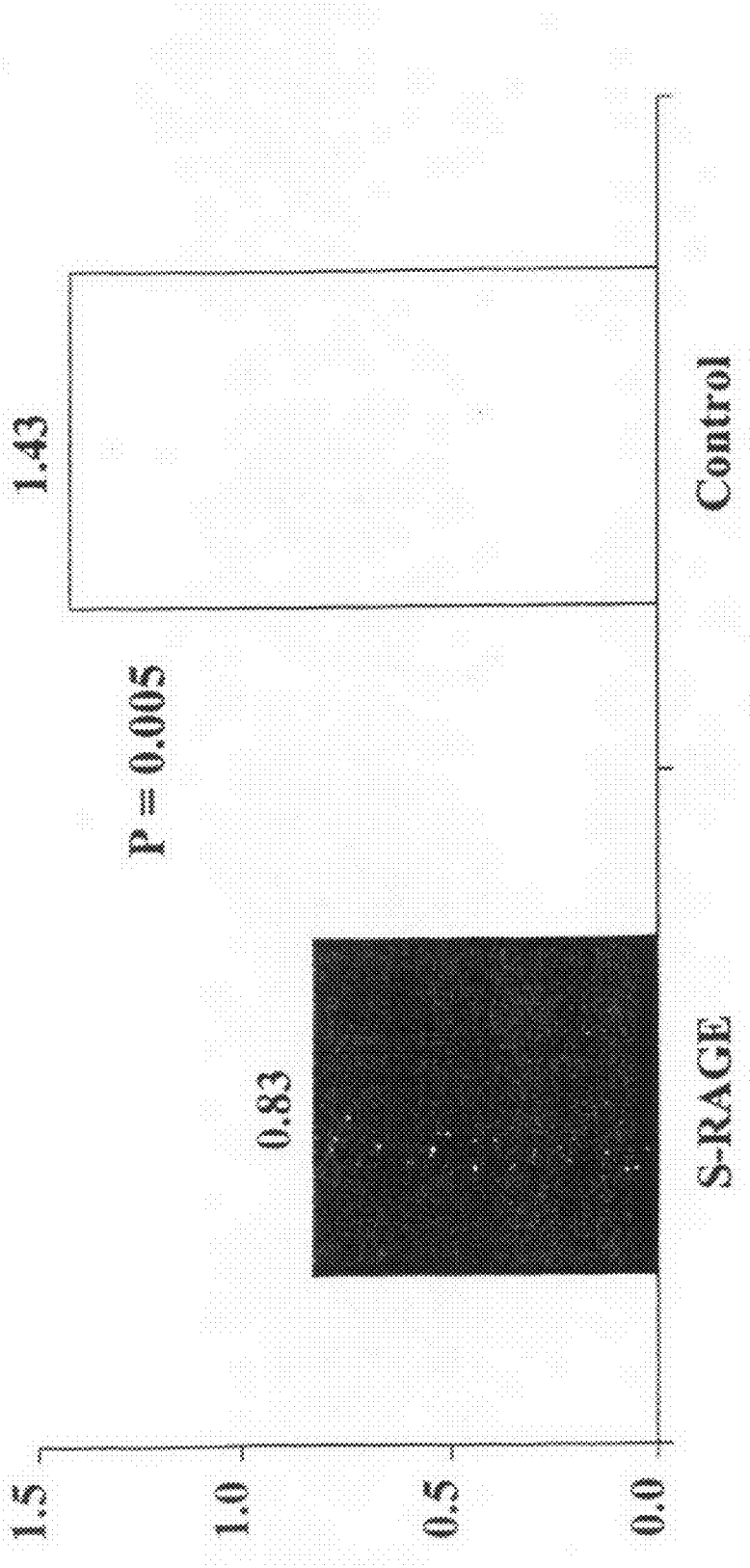

METHOD FOR INHIBITING NEW TISSUE GROWTH IN BLOOD VESSELS IN A PATIENT SUBJECTED TO BLOOD VESSEL INJURY

This application is a continuation of U.S. Ser. No. 11/894,809, filed Aug. 20, 2007 now U.S. Pat. No. 7,732,400, now allowed, which is a continuation of U.S. Ser. No. 09/687,528, filed Oct. 13, 2000, now abandoned, the contents of each of which are hereby incorporated by reference.

BACKGROUND OF THE INVENTION

Throughout this application, various publications are referenced by number. Full citations for these publications may be found listed at the end of the specification immediately preceding the claims. The disclosures of these publications in their entireties are hereby incorporated by reference into this application in order to more fully describe the state of the art as known to those skilled therein as of the date of the invention described and claimed herein.

It is well-established that the incidence of diabetes is rising sharply in the Unites States and worldwide. Despite aggressive efforts to optimize and achieve strict control of hyperglycemia in affected subjects, the leading cause of death in patients with diabetes remains coronary artery disease (70% of all case fatalities).

In persons with coronary artery stenosis, one form of therapeutic intervention involves percutaneous revascularization (angioplasty) (PTCA). Prior registry data demonstrated that between 15-25% of patients undergoing PTCA have a history of diabetes mellitus. Although there have been great strides in the field of cardiovascular medicine in the last 15 years, there has been little done to improve the outcomes of persons with diabetes and atherosclerotic coronary artery disease. This was most recently clearly demonstrated in a number of recent studies (1-3), including the BARI investigations and the studies comparing the NHANES I and NHANES II cohorts. Comparing these two epidemiologic surveys, investigators showed a marked improvement in cardiovascular and rated outcomes for patients without a history of diabetes. There was an overall 21.1% and 12.6% risk reduction in all cause mortality in non-diabetic men and women, respectively. In contradistinction, there was only a 1.2% reduction in all cause mortality for diabetic men, and a surprising 15.2% increase in all cause mortality for diabetic women. Similar to the NHANE epidemiologic surveys, patients with diabetes seem to be a higher risk cohort of patients following PTCA interventions. Another example of the heightened risk of vascular disease in diabetes of medical urgency concerns the response to angioplasty as illustrated by the BARI study in which patients with diabetes displayed poorer results from angioplasty than from bypass surgery largely because of accelerated restenosis. From the results of these studies, the view has emerged that diabetic patients are at a heightened risk for angiographic and clinical restenosis, late myocardial infarction, late mortality, and need for future revascularization procedures. In data retrieved from one of our institutes (Mid America Heart Institute) involving over 25,000 patients, we found that diabetic patients have a nearly two-fold increase in in-hospital mortality following both elective and urgent PTCA interventions. The in-hospital mortality rate was 0.8% compared with 1.4% for non-diabetic and diabetic patients undergoing elective PTCA, respectively; p<0.001. Similarly, the in-hospital morality rate was 6.9% compared with 12.7% for non-diabetic and diabetic patients undergoing PTCA for acute myocardial infarction, p<0.001.

SUMMARY OF THE INVENTION

This invention provides for a method for inhibiting new tissue growth in blood vessels in a subject, wherein the subject experienced blood vessel injury, which comprises administering to the subject a pharmaceutically effective amount of an inhibitor of receptor for advanced glycation endproduct (RAGE) so as to inhibit new tissue growth in the subject's blood vessels.

The invention also provides for method for inhibiting neointimal formation in blood vessels in a subject, wherein the subject experienced blood vessel injury, which comprises administering to the subject a pharmaceutically effective amount of an inhibitor of receptor for advanced glycation endproduct (RAGE) so as to inhibit neointimal formation in the subject's blood vessels.

The invention also provides a method for preventing exaggerated restenosis in a diabetic subject which comprises administering to the subject a pharmaceutically effective amount of an inhibitor of receptor for advanced glycation endproduct (RAGE) so as to prevent exaggerated restenosis in the subject.

BRIEF DESCRIPTION OF THE FIGURES

FIG. 1. Blockade, using soluble (s) RAGE, suppresses neointimal expansion after carotid artery injury. Fatty Zucker rats were subjected to carotid artery injury as described herein. Rats received either sRAGE or vehicle, albumin, one day prior to injury, and the subsequent 6 days after injury. Rats were sacrificed on day 21 after injury and histologic analysis performed for assessment of neointimal area. Results are reported in $mm^2$.

FIG. 2. Blockade of RAGE, using sRAGE, results in decreased neointima/media ratio after carotid artery injury. Fatty Zucker rats were subjected to carotid artery injury as described above. Rats received either sRAGE or vehicle, albumin, one day prior to injury, and the subsequent 6 days after injury. Rats were sacrificed on day 21 after injury and histologic analysis performed for assessment of neointimal and medial area. Results are reported as the ratio of the neointimal to medial ration.

DETAILED DESCRIPTION OF THE INVENTION

This invention provides for a method for inhibiting new tissue growth in blood vessels in a subject, wherein the subject experienced blood vessel injury, which comprises administering to the subject a pharmaceutically effective amount of an inhibitor of receptor for advanced glycation endproduct (RAGE) so as to inhibit new tissue growth in the subject's blood vessels.

The invention also provides for method for inhibiting neointimal formation in blood vessels in a subject, wherein the subject experienced blood vessel injury, which comprises administering to the subject a pharmaceutically effective amount of an inhibitor of receptor for advanced glycation endproduct (RAGE) so as to inhibit neointimal formation in the subject's blood vessels.

The invention also provides a method for preventing exaggerated restenosis in a diabetic subject which comprises administering to the subject a pharmaceutically effective amount of an inhibitor of receptor for advanced glycation endproduct (RAGE) so as to prevent exaggerated restenosis in the subject.

In one embodiment of the invention, the subject is a non-human animal, a transgenic non-human animal or a human.

In another embodiment of the invention, the subject has undergone an angioplasty procedure or has undergone surgery to implant a stent in a blood vessel.

In another embodiment of the invention, the inhibitor is a molecule having a molecular weight from about 500 daltons to about 100 kilodaltons. In another embodiment of the invention, the inhibitor is an organic molecule or an inorganic molecule. In another embodiment of the invention, the inhibitor is a polypeptide or a nucleic acid molecule. In another embodiment of the invention, the inhibitor is soluble receptor for advanced glycation endproduct.

In another embodiment of the invention, the inhibitor is an antibody which specifically binds to receptor for advanced glycation endproduct.

In one embodiment of the invention, the inhibitor is administered to the subject by bolus injection, intraperitoneal injection, i.v., oral administration, topical application to the blood vessel, coating of a device to be placed within the subject, coating of an instrument used during a procedure upon the subject which results in blood vessel injury, or contacting blood of the subject during extracorporeal circulation.

In another embodiment of the invention, the device to be placed within the subject is a stent or an angioplasty balloon.

In another embodiment of the invention, the inhibitor is administered to the subject at a rate from about 2 µg/kg/hr to about 100 µg/kg/hr.

In another embodiment of the invention, the inhibitor is coated onto a stent used during an angioplasty of the subject.

In another embodiment of the invention, the subject is suffering from diabetes, acute thrombotic stroke, venous thrombosis, myocardial infarction, unstable angina, abrupt closure following angioplasty or stent placement, or thrombosis as a result of peripheral vascular surgery.

In another embodiment of the invention, the administering is carried out via injection, oral administration, topical administration, adenovirus infection, liposome-mediated transfer, intravenous administration, intraperitoneal injection, bolus injection, topical application to the blood vessel cells of the subject, or microinjection.

The present invention also provides for a method for determining whether a compound inhibits new tissue growth in a blood vessel in a subject, wherein the blood vessel has been subjected to injury, which comprises: (a) administering the compound to a non-human animal which has undergone blood vessel injury; (b) determining whether the non-human animal has inhibited new tissue growth or inhibited neointimal formation in said blood vessel when compared to new tissue growth or neointimal formation in an injured blood vessel in an identical non-human animal which was not administered the test compound; wherein a decrease in new tissue growth or a decrease in neointimal formation in the non-human animal to which the compound was administered indicates that the test compound inhibits new tissue growth or neointimal formation in the injured blood vessel in the subject.

In one embodiment of the invention, the compound is an organic molecule or an inorganic molecule. In another embodiment of the invention, the compound is a polypeptide or a nucleic acid molecule. In another embodiment of the invention, the compound is soluble receptor for advanced glycation endproduct. In another embodiment of the invention; the compound is an antibody which specifically binds to receptor for advanced glycation endproduct.

In one embodiment of the invention, the non-human animal is a pig, a bovine, a canine, a rat, a mouse, a sheep or a primate. In another embodiment of the invention, the non-human animal is a non-human diabetic animal model. In another embodiment of the invention, the non-human animal is a Zucker fatty rat.

In one embodiment of the invention, the subject is a human.

In one embodiment of the invention, the inhibitor is a molecule having a molecular weight from about 500 daltons to about 100 kilodaltons. In another embodiment of the invention, the inhibitor is an organic molecule or an inorganic molecule. In another embodiment of the invention, the inhibitor is a polypeptide or a nucleic acid molecule. In another embodiment of the invention, the inhibitor is soluble receptor for advanced glycation endproduct. In another embodiment of the invention, the inhibitor is an antibody which specifically binds to receptor for advanced glycation endproduct.

In one embodiment of the invention, the inhibitor of receptor for advanced glycation endproduct (RAGE) is soluble receptor for advanced glycation endproduct (RAGE).

The present invention provides for a method for determining whether a compound inhibits new tissue growth in a blood vessel in a subject, wherein the blood vessel has been subjected to injury, which comprises: (a) administering the compound to a non-human animal which has undergone blood vessel injury (e.g., has undergone a stent implant or an angioplasty); (b) determining whether the non-human animal has inhibited new tissue growth or inhibited neointimal formation in said blood vessel when compared to new tissue growth or neointimal formation in an injured blood vessel in an identical non-human animal which was not administered the test compound; wherein a decrease in new tissue growth or a decrease in neointimal formation in the non-human animal to which the compound was administered indicates that the test compound inhibits new tissue growth or neointimal formation in the injured blood vessel in the subject.

In one embodiment of the invention, the blood vessel of the subject is a macrovascular structure. For example, the blood vessel is the aorta, the carotid artery, or a femoral artery or vein.

In one embodiment of the invention, the compound is a molecule having a molecular weight from about 500 daltons to about 100 kilodaltons. In one embodiment of the invention, the compound is an organic molecule or an inorganic molecule. In one embodiment of the invention, the compound is a polypeptide or a nucleic acid molecule.

In one embodiment of the invention, the inhibitor of RAGE is soluble RAGE.

DEFINITIONS

As used herein, "treating" encompasses management and care of a patient for the purpose of combating the disease, condition, or disorder and includes the administration of a compound of the present invention to prevent the onset of the symptoms or complications, alleviating the symptoms or complications, or eliminating the disease, condition, or disorder.

As used herein, "neointimal formation" encompasses new tissue growth in a blood vessel.

"DNA sequence" is a linear sequence comprised of any combination of the four DNA monomers, i.e., nucleotides of adenine, guanine, cytosine and thymine, which codes for genetic information, such as a code for an amino acid, a promoter, a control or a gene product. A specific DNA sequence is one which has a known specific function, e.g., codes for a particular polypeptide, a particular genetic trait or affects the expression of a particular phenotype.

"Genotype" is the genetic constitution of an organism.

"Phenotype" is a collection of morphological, physiological and biochemical traits possessed by a cell or organism that results from the interaction of the genotype and the environment.

"Phenotypic expression" is the expression of the code of a DNA sequence or sequences which results in the production of a product, e.g., a polypeptide or protein, or alters the expression of the zygote's or the organisms natural phenotype.

In another embodiment, the administering is carried out via injection, oral administration, topical administration, adenovirus infection, liposome-mediated transfer, topical application to the cells of the subject, or microinjection.

In the practice of any of the methods of the invention or preparation of any of the pharmaceutical compositions an "therapeutically effective amount" is an amount which is capable of alleviating the symptoms of the disorder of memory or learning in the subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

The "non-human animals" of the invention include vertebrates such as rodents, non-human primates, sheep, dog, cow, amphibians, reptiles, etc. Preferred non-human animals are selected from the rodent family including rat and mouse, most preferably mouse.

U.S. Pat. No. 5,879,380, issued Mar. 9, 1999 to Kalmann, et al., entitled "Assembly for treating blood vessels and a method therefor" is incorporated herein by reference. This patent describes some procedures which are undertaken to treat stenosis in patients and which lead to blood vessel injury.

U.S. Pat. No. 5,843,102, issued Dec. 1, 1998, to Kalmann, et al., entitled "Instrument for loosening and cutting through the intima of a blood vessel, and a method therefor" is incorporated herein by reference. This patent describes some procedures which are undertaken to treat stenosis in patients and which lead to blood vessel injury.

U.S. Pat. No. 5,591,225, issued Jan. 7, 1997 to Okuda, entitled "Composite artificial blood vessel" is hereby incorporated herein by reference. This patent describes an artificial blood vessel which could be coated or implanted with the inhibitors described herein in order to carry out the methods for inhibiting neointimal formation in an injured blood vessel of a subject.

The present invention provides a method of treatment for patients undergoing a procedure which causes tissue injury to the patients' blood vessels (e.e.g, angioplasty or stent placement). Said treatment is a therapy comprising administration of an inhibitor of RAGE, wherein the inhibitor inhibits the binding of RAGE to its ligand. It is known that RAGE binds to several ligands, such as AGEs and certain proteins which are family members of the S100/calgranulin family (e.g. EN-RAGE, S100B).

In one embodiment, the subject is suffering from diabetes, acute thrombotic stroke, venous thrombosis, myocardial infarction, unstable angina, abrupt closure following angioplasty or stent placement, or thrombosis as a result of peripheral vascular surgery.

U.S. Pat. No. 6,071,514, issued Jun. 6, 2000 to Grinell, et al., entitled "Methods for treating thrombotic disorders" is is hereby incorporated herein by reference. This patent describes methods for treating thrombotic disorders. It also describes methods of administering compounds to subjects suffering from such disorders.

Nucleotide and Amino Acid Sequences of RAGE

The nucleotide and protein (amino acid) sequences for RAGE (both human and murine and bovine) are known. The following references which recite these sequences are incorporated by reference:

Schmidt et al, J. Biol. Chem., 267:14987-97, 1992

Neeper et al, J. Biol. Chem., 267:14998-15004, 1992

RAGE sequences (DNA sequence and translation) from bovine, murine and *homo sapien* are listed hereinbelow. These sequences are available from GenBank as are other sequences of RAGE from other species:

LOCUS BOVRAGE 1426 bp mRNA MAM 09 DEC 1993 DEFINITION Cow receptor for advanced glycosylation end products (RAGE) mRNA, complete cds.

ACCESSION M91212VERSION M91212.1 GI: 163650

KEYWORDS RAGE; cell surface receptor.

SOURCE *Bos taurus* cDNA to mRNA. ORGANISM *Bos taurus* Eukaryota; Metazoa; Chordata; Craniata; Vertebrata; Euteleostomi; Mammalia; Eutheria; Cetartiodactyla; Ruminantia; Pecora; Bovoidea; Bovidae; Bovinae; *Bos*.

REFERENCE 1 (bases 1 to 1426) AUTHORS Neeper, M., Schmidt, A. M., Brett, J., Yan, S. D., Wang, F., Pan, Y. C., Elliston, K., Stern, D. and Shaw, A. TITLE Cloning and expression of a cell surface receptor for advanced glycosylation end products of proteins JOURNAL J. Biol. Chem. 267, 14998-15004 (1992)

MEDLINE 92340547 REFERENCE 2 (bases 1 to 1426) AUTHORS Shaw, A. TITLE Direct Submission JOURNAL Submitted (15 APR 1992) A. Shaw, Department of Cellular and Molecular Biology, Merck Sharp and Dohme Research Laboratories, West Point, Pa. 19486

USAFEATURES Location/Qualifiers source 1 . . . 1426/ organism="*Bos taurus*"/db_xref="taxon:9913"/ tissue_type="lung" CDS 10 . . . 1260/ standardname="RAGE"/codon_start=1/product="receptor for advanced glycosylation end products"/ protein_id="AAA03575.1"/db_xref="GI:163651"

/translation="

(SEQ ID NO: 1)

MAAGAVVGAWMLVLSLGGTVTGDQNITARIGKPLVLNCKGAPKKPPQQ

LEWKLNTGRTEAWKVLSPQGDPWDSVARVLPNGSLLLPAVGIQDEGTF

RCRATSRSGKETKSNYRVRVYQIPGKPEIVDPASELMAGVPNKVGTCV

SEGGYPAGTLNWLLDGKTLIPDGKGVSVKEETKRHPKTGLFTLHSELM

VTPARGGALHPTFSCSFTPGLPRRRALHTAPIQLRVWSEHRGGEGPNV

DAVPLKEVQLVVEPEGGAVAPGGTVTLTCEAPAQPPPQIHWIKDGRPL

PLPPGPMLLLPEVGPEDQGTYSCVATHPSHGPQESRAVSVTIIETGEE

GTTAGSVEGPGLETLALTLGILGGLGTVALLIGVIVWHRRRQRKGQER

KVPENQEEEEERAELNQPEEPEAAESSTGGP polyA_signal 1406 . . . 1411 polyA_site 1426

BASE COUNT 322 a 429 c 440 g 235 t

Origin (SEQ ID NO: 2)

```
   1 cggagaagga tggcagcagg ggcagtggtc ggagcctgga tgctagtcct cagtctgggg
  61 gggacagtca cggggacca aaacatcaca gcccggatcg ggaagccact ggtgctgaac
 121 tgcaaggag cccccaagaa accacccag cagctggaat ggaaactgaa cacaggccgg
 181 acagaagctt ggaaagtcct gtctccccag ggagacccct gggatagcgt ggctcgggtc
 241 ctccccaacg gctccctcct cctgccggct gttgggatcc aggatgaggg gactttccgg
 301 tgccgggcaa cgagccggag cggaaggag accaagtcta actaccgagt ccgagtctat
 361 cagattcctg ggaagccaga aattgttgat cctgcctctg aactcatggc tggtgtcccc
 421 aataaggtgg ggacatgtgt gtccgagggg ggctaccctg cagggactct taactggctc
 481 ttggatggga aaactctgat tcctgatggc aaaggagtgt cagtgaagga agagaccaag
 541 agacacccaa agacagggct tttcacgctc cattcggagc tgatggtgac cccagctcgg
 601 ggaggagctc tccaccccac cttctcctgt agcttcaccc ctggccttcc ccggcgccga
 661 gccctgcaca cggcccccat ccagctcagg gtctggagtg agcaccgagg tggggagggc
 721 cccaacgtgg acgctgtgcc actgaaggaa gtccagttgg tggtagagcc agaaggggga
 781 gcagtagctc ctggtggtac tgtgaccttg acctgtgaag ccccgccca gcccccacct
 841 caaatccact ggatcaagga tggcaggcc ctgcccttc ccctggccc catgctgctc
 901 ctcccagagg tagggcctga ggaccaggga acctacagtt gtgtggccac ccatccagc
 961 catgggcccc aggagagccg tgctgtcagc gtcacgatca tcgaaacagg cgaggagggg
1021 acgactgcag gctctgtgga agggccgggg ctggaaaccc tagccctgac cctgggatc
1081 ctggaggcc tggggacagt cgccctgctc attggggtca tcgtgtggca tcgaaggcgg
1141 caacgcaaag gacaggagag gaaggtcccg gaaaaccagg aggaggaaga ggaggagaga
1201 gcggaactga accagccaga ggagcccgag gcggcagaga gcagcacagg agggccttga
1261 ggagcccacg gccagacccg atccatcagc cccttttctt ttcccacact ctgttctggc
1321 cccagaccag ttctcctctg tataatctcc agcccacatc tcccaaactt tcttccacaa
1381 ccagagcctc ccacaaaaag tgatgagtaa acacctgcca cattta//
```

LOCUS HUMRAGE 1391 bp mRNA PRI 09 DEC 1993
DEFINITION Human receptor for advanced glycosylation end products (RAGE) mRNA, partial cds.
ACCESSION M91211 VERSION M91211.1 GI:190845
KEYWORDS RAGE; cell surface receptor.
SOURCE *Homo sapiens* cDNA to mRNA.
ORGANISM *Homo sapiens* Eukaryota; Metazoa; Chordata; Craniata; Vertebrata; Euteleostomi; Mammalia; Eutheria; Primates; Catarrhini; Homimidae; *Homo*.
REFERENCE 1 (bases 1 to 1391)
AUTHORS Neeper, M., Schmidt, A. M., Brett, J., Yan, S. D., Wang, F., Pan, Y. C., Elliston, K., Stern, D. and Shaw, A.
TITLE Cloning and expression of a cell surface receptor for advanced glycosylation end products of proteins
JOURNAL J. Biol. Chem. 267, 14998-15004 (1992)
MEDLINE 92340547
REFERENCE 2 (bases 1 to 1391)
AUTHORS Shaw, A.
TITLE Direct Submission
JOURNAL Submitted (15 APR 1992) A. Shaw, Department of Cellular and Molecular Biology, Merck Sharp and Dohme Research Laboratories, West Point, Pa. 19486 USA FEATURES Location/Qualifiers source 1 . . . 1391/ organism="*Homo sapiens*"/db_xref="taxon:9606"/ tissue_type="lung" CDS <1 . . . 1215/ standard_name="RAGE"/codon_start=1/product="receptor for advanced glycosylation end products"/ protein_id="AAA03574.1"/db_xref="GI:190846" /translation="

(SEQ ID NO: 3)
GAAGTAVGAWVLVLSLWGAVVGAQNITARIGEPLVLKCKGAPKKPPQ

RLEWKLNTGRTEAWKVLSPQGGGPWDSVARVLPNGSLFLPAVGIQDE

GIFRCRAMNRNGKETKSNYRVRVYQIPGKPEIVDSASELTAGVPNKV

GTCVSEGSYPAGTLSWHLDGKPLVPNEKGVSVKEQTRRHPETGLFTL

QSELMVTPARGGDPRPTFSCSFSPGLPRHRALRTAPIQPRVWEPVPL

EEVQLVVEPEGGAVAPGGTVTLTCEVPAQPSPQIHWMKDGVPLPLPP

SPVLILPEIGPQDQGTYSCVATHSSHGPQESRAVSISIIEPGEEGPT

AGSVGGSGLGTLALALGILGGLGTAALLIGVILWQRRQRRGEERKAP

ENQEEEEERAELNQSEEPEAGESSTGGP polyA_signal 1368 . . . 1373 polyA_site 1391
BASE COUNT 305 a 407 c 418 g 261 t Origin (SEQ ID NO: 4)

```
   1 ggggcagccg aacagcagt tggagcctgg gtgctggtcc tcagtctgtg ggggcagta
  61 gtaggtgctc aaaacatcac agcccggatt ggcgagccac tggtgctgaa gtgtaagggg
 121 gcccccaaga aaccaccca gcggctgaa tggaaactga acacaggccg gacagaagct
 181 tggaaggtcc tgtctcccca gggaggaggc ccctgggaca gtgtggctcg tgtccttccc
 241 aacggctccc tcttccttcc ggctgtcggg atccaggatg aggggatttt ccggtgcagg
 301 gcaatgaaca ggaatggaaa ggagaccaag tccaactacc gagtccgtgt ctaccagatt
 361 cctgggaagc cagaaattgt agattctgcc tctgaactca cggctggtgt tcccaataag
 421 gtggggacat gtgtgtcaga gggaagctac cctgcaggga ctcttagctg gcacttggat
 481 gggaagcccc tggtgcctaa tgagaaggga gtatctgtga aggaacagac caggagacac
 541 cctgagacag ggctcttcac actgcagtcg gagctaatgg tgacccagc ccggggagga
 601 gatccccgtc ccaccttctc ctgtagcttc agcccaggcc ttccccgaca ccgggccttg
 661 cgcacagccc ccatccagcc ccgtgtctgg gagcctgtgc ctctggagga ggtccaattg
 721 gtggtggagc cagaaggtgg agcagtagct cctggtggaa ccgtaaccct gacctgtgaa
 781 gtccctgccc agccctctcc tcaaatccac tggatgaagg atggtgtgcc cttgcccctt
 841 cccccccagcc ctgtgctgat cctccctgag atagggcctc aggaccaggg aacctacagc
 901 tgtgtggcca cccattccag ccacgggccc caggaaagcc gtgctgtcag catcagcatc
 961 atcgaaccag gcgaggaggg gccaactgca ggctctgtgg gaggatcagg gctgggaact
1021 ctagccctgg ccctggggat cctgggaggc ctggggacag ccgccctgct cattgggtc
1081 atcttgtggc aaaggcggca acgccgagga gaggagagga aggccccaga aaaccaggag
1141 gaagaggagg agcgtgcaga actgaatcag tcggaggaac ctgaggcagg cgagagtagt
1201 actgagggc cttgagggc ccacagacag atcccatcca tcagctccct tttcttttc
1261 ccttgaactg ttctggcctc agaccaactc tctcctgtat aatctctctc ctgtataacc
1321 ccaccttgcc aagctttctt ctacaaccag agcccccac aatgatgatt aaacacctga
1381 cacatcttgc a//
```

LOCUS MUSRECEP 1348 bp mRNA ROD 23 AUG 1994
DEFINITION Mouse receptor for advanced glycosylation end products (RAGE) gene, complete cds.
ACCESSION L33412VERSION L33412.1 GI:532208
KEYWORDS receptor for advanced glycosylation end products.
SOURCE *Mus musculus* (strain BALB/c, sub_species *domesticus*) (library: lambda gt10) male adult lung cDNA to mRNA.
ORGANISM *Mus musculus* Eukaryota; Metazoa; Chordata; Craniata; Vertebrata; Euteleostomi; Mammalia; Eutheria; Rodentia; Sciurognathi; Muridae; Murinae; *Mus*.
REFERENCE 1 (bases 1 to 1348)
AUTHORS Lundh, E. R., Morser, J., McClary, J. and Nagashima, M.
TITLE Isolation and characterization of cDNA encoding the murine and rat homologues of the mammalian receptor for advanced glycosylation end products
JOURNAL UnpublishedCOMMENT On Aug. 24, 1994 this sequence version replaced gi:496146.
FEATURES Location/Qualifiers source 1 . . . 1348/ organism="*Mus musculus*"/strain="BALB/c"/ sub_species="*domesticus*"/db_xref="taxon:10090"/ sex="male"/tissue_type="lung"/dev_stage="adult"/ tissue_lib="lambda gt10" gene 6 . . . 1217/gene="RAGE" CDS 6 . . . 1217/gene="RAGE"/codon_start=1/ product="receptor for advanced glycosylation end products"/ protein_id="AAA40040.1"/db_xref="GI:532209" /translation="

(SEQ ID NO: 5)
MPAGTAARAWVLVLALWGAVAGGQNITARIGEPLVLSCKGAPKKPPQ

QLEWKLNTGRTEAWKVLSPQGGPWDSVAQILPNGSLLLPATGIVDEG

TFRCRATNRRGKEVKSNYRVRVYQIPGKPEIVDPASELTASVPNKVG

TCVSEGSYPAGTLSWHLDGKLLIPDGKETLVKEETRRHPETGLFTLR

SELTVIPTQGGTTHPTFSCSFSLGLPRRRPLNTAPIQLRVREPGPPE

GIQLLVEPEGGIVAPGGTVTLTCAISAQPPPQVHWIKDGAPLPLAPS

PVLLLPEVGHADEGTYSCVATHPSHGPQESPPVSIRVTETGDEGPAE

GSVGESGLGTLALALGILGGLGVVALLVGAILWRKRQPRREERKAPE

SQEDEEERAELNQSEEAEMPENGAGGP polyA_site 1333
BASE COUNT 301 a 394 c 404 g 249 t

Origin (SEQ ID NO: 6)

```
   1 gcaccatgcc agcggggaca gcagctagag cctgggtgct ggttcttgct ctatggggag
  61 ctgtagctgg tggtcagaac atcacagccc ggattggaga gccacttgtg ctaagctgta
 121 aggggggcccc taagaagccg ccccagcagc tagaatggaa actgaacaca ggaagaactg
 181 aagcttggaa ggtcctctct ccccagggag gccctggga cagcgtggct caaatcctcc
 241 ccaatggttc cctcctcctt ccagccactg gaattgtcga tgaggggacg ttccggtgtc
 301 gggcaactaa caggcgaggg aaggaggtca agtccaacta ccgagtccga gtctaccaga
 361 ttcctgggaa gccagaaatt gtggatcctg cctctgaact cacagccagt gtccctaata
 421 aggtggggac atgtgtgtct gagggaagct accctgcagg gacccttagc tggcacttag
 481 atgggaaact tctgattccc gatggcaaag aaacactcgt gaaggaagag accaggagac
 541 accctgagac gggactcttt acactgcggt cagagctgac agtgatcccc acccaaggag
 601 gaaccaccca tcctaccttc tcctgcagtt tcagcctggg ccttccccgg cgcagacccc
 661 tgaacacagc ccctatccaa ctccgagtca gggagcctgg gcctccagag ggcattcagc
 721 tgttggttga gcctgaaggt ggaatagtcg ctcctggtgg gactgtgacc ttgacctgtg
 781 ccatctctgc ccagccccct cctcaggtcc actggataaa ggatggtgca cccttgcccc
 841 tggctcccag ccctgtgctg ctcctccctg aggtggggca cgcggatgag ggcacctata
 901 gctgcgtggc cacccaccct agccacggac ctcaggaaag ccctcctgtc agcatcaggg
 961 tcacagaaac cggcgatgag gggccagctg aaggctctgt gggtgagtct gggctgggta
1021 cgctagccct ggccttgggg atcctgggag gcctgggagt agtagccctg ctcgtcgggg
1081 ctatcctgtg gcgaaaacga caacccaggc gtgaggagag gaaggccccg gaaagccagg
1141 aggatgagga ggaacgtgca gagctgaatc agtcagagga gcggagatg ccagagaatg
1201 gtgccggggg accgtaagag cacccagatc gagcctgtgt gatggcccta gagcagctcc
1261 cccacattcc atcccaattc ctccttgagg cacttccttc tccaaccaga gcccacatga
1321 tccatgctga gtaaacattt gatacggc//
```

Inhibitors of RAGE:

Inhibitors of RAGE include any molecule which, when introduced into a cell or a subject, is capable of inhibiting the biological activity of RAGE. For example, one such inhibitor would be able to inhibit the activity of RAGE as described: the binding of RAGE to AGEs in the blood or the binding of RAGE to its ligands, for example, EN-RAGE, S100B, or a member of the S100/calgranulin protein family). The S100/calgranulin protein family are characterized by containing EF hand loops and have been shown to bind RAGE.

Examples of an inhibitor of RAGE activity are soluble RAGE, an antibody which specifically binds to RAGE, a truncated version of RAGE which is capable of acting as a competitive inhibitor of RAGE. A fragment of RAGE which includes the amyloid beta peptide binding portion of RAGE and introduced into the cell or subject as a soluble polypeptide. Other types of inhibitors would be known to one of skill in the art. For example, a small molecule could be prepared which mimics the amyloid beta peptide binding region of RAGE and administered alone as an inhibitor.

Pharmaceutical Compositions and Carriers

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of protein compositions and compounds together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility: stability, rate of in vivo release, and rate of in vivo clearance of the compound or composition. The choice of compositions will depend on the physical and chemical properties of the compound.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the compound of the invention may be "labeled" by association with a detectable marker substance (e.g., radiolabeled with $^{125}$I or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment the compound of the present invention is associated with a pharmaceutical carrier which includes a pharmaceutical composition. The pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

The following U.S. Patents are hereby incorporated by reference:

| PAT. NO. | Title |
| --- | --- |
| 6,120,533 | Stent delivery system for a radioisotope stent |
| 6,093,141 | Stereotactic radiotreatment and prevention |
| 6,080,190 | Intraluminal stent |
| 6,077,273 | Catheter support for stent delivery |
| 6,074,362 | Catheter system having imaging, balloon angioplasty, and stent deployment capabilities, and methods of use for guided stent deployment |
| 6,071,514 | Methods for treating thrombotic disorders |
| 6,071,286 | Combination angioplasty balloon/stent deployment device |
| 6,059,809 | Protective angioplasty device |
| 6,053,913 | Rapid exchange stented balloon catheter having ablation capabilities |
| 6,027,509 | Stent retrieval device |
| 6,027,508 | Stent retrieval device |
| 6,015,430 | Expandable stent having a fabric liner |
| 6,011,995 | Endovascular device for hyperthermia and angioplasty and method for using the same |
| 6,004,339 | Balloon catheter with multiple distensibilities |
| 5,980,485 | Pressure-sensitive balloon catheter |
| 5,976,153 | Stent delivery catheter system |
| 5,957,971 | Intraluminal stent |
| 5,944,735 | Process for stent compression |
| 5,910,145 | Stent delivery catheter system |
| 5,902,299 | Cryotherapy method for reducing tissue injury after balloon angioplasty or stent implantation |
| 5,893,867 | Stent positioning apparatus and method |
| 5,893,840 | Releasable microcapsules on balloon catheters |
| 5,891,133 | Apparatus for laser-assisted intra-coronary transmyocardial revascularization and other applications |
| 5,871,437 | Radioactive stent for treating blood vessels to prevent restenosis |
| 5,868,755 | Sheath retractor mechanism and method |
| 5,855,563 | Method and apparatus for sequentially performing multiple intraluminal procedures |

-continued

| PAT. NO. | Title |
|---|---|
| 5,854,223 | S-DC28 as an antirestenosis agent after balloon injury |
| 5,849,034 | Intraluminal stent |
| 5,843,163 | Expandable stent having radioactive treatment means |
| 5,836,952 | Hand-held stent crimper |
| 5,833,982 | Modified factor VII |
| 5,814,061 | Rapid exchange stent delivery balloon catheter |
| 5,800,507 | Intraluminal stent |
| 5,799,384 | Intravascular radially expandable stent |
| 5,797,887 | Medical device with a surface adapted for exposure to a blood stream which is coated with a polymer containing a nitrosyl-containing organo-metallic compound which releases nitric oxide from the coating to mediate platelet aggregation |
| 5,792,144 | Stent delivery catheter system |
| 5,776,141 | Method and apparatus for intraluminal prothesis delivery |
| 5,766,192 | Atherectomy, angioplasty and stent method and apparatus |
| 5,755,776 | Permanent expandable intraluminal tubular stent |
| 5,749,848 | Catheter system having imaging, balloon angioplasty, and stent deployment capabilities, and method of use for guided stent deployment |
| 5,749,825 | Means method for treatment of stenosed arterial bifurcations |
| 5,746,766 | Surgical stent |
| 5,746,764 | Stent compression instrument |
| 5,743,874 | Integrated catheter for balloon angioplasty and stent delivery |
| 5,738,674 | Stent loading mechanism |
| 5,730,698 | Balloon expandable temporary radioisotope stent system |
| 5,722,979 | Pressure assisted ultrasonic balloon catheter and method of using same |
| 5,702,419 | Expandable, intraluminal stents |
| 5,690,642 | Rapid exchange stent delivery balloon catheter |
| 5,669,932 | Means for accurately positioning an expandable stent |

The disclosures of publications referenced in this application in their entireties are hereby incorporated by reference into this application in order to more fully describe the state of the art as known to those skilled therein as of the date of the invention described and claimed herein.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Blockade of Receptor for Age (Rage) Suppresses Neointimal Formation in Diabetic Rats Subjected to Carotid Artery Injury It is well-established that the incidence of diabetes is rising sharply in the Unites States and worldwide. Despite aggressive efforts to optimize and achieve strict control of hyperglycemia in affected subjects, the leading cause of death in patients with diabetes remains coronary artery disease (70% of all case fatalities). In persons with coronary artery stenosis, one form of therapeutic intervention involves percutaneous revascularization (angioplasty) (PTCA). Prior registry data demonstrated that between 15-25% of patients undergoing PTCA have a history of diabetes mellitus.

Although there have been great strides in the field of cardiovascular medicine in the last 15 years, there has been little done to improve the outcomes of persons with diabetes and atherosclerotic coronary artery disease. This was most recently clearly demonstrated in a number of recent studies (1-3), including the BARI investigations and the studies comparing the NHANES I and NHANES II cohorts. Comparing these two epidemiologic surveys, investigators showed a marked improvement in cardiovascular and rated outcomes for patients without a history of diabetes. There was an overall 21.1% and 12.6% risk reduction in all cause mortality in non-diabetic men and women, respectively. In contradistinction, there was only a 1.2% reduction in all cause mortality for diabetic men, and a surprising 15.2% increase in all cause mortality for diabetic women. Similar to the NHANE epidemiologic surveys, patients with diabetes seem to be a higher risk cohort of patients following PTCA interventions.

Another example of the heightened risk of vascular disease in diabetes of medical urgency concerns the response to angioplasty as illustrated by the BARI study in which patients with diabetes displayed poorer results from angioplasty than from bypass surgery largely because of accelerated restenosis. From the results of these studies, the view has emerged that diabetic patients are at a heightened risk for angiographic and clinical restenosis, late myocardial infarction, late mortality, and need for future revascularization procedures.

In data retrieved from one of our institutes (Mid America Heart Institute) involving over 25,000 patients, we found that diabetic patients have a nearly two-fold increase in in-hospital mortality following both elective and urgent PTCA interventions. The in-hospital mortality rate was 0.8% compared with 1.4% for non-diabetic and diabetic patients undergoing elective PTCA, respectively; $p<0.001$. Similarly, the in-hospital morality rate was 6.9% compared with 12.7% for non-diabetic and diabetic patients undergoing PTCA for acute myocardial infarction, $p<0.001$.

In order to dissect the contribution of multiple, diabetes-associated factors in the response to arterial injury, we developed a model of exaggerated neointimal formation in rats with type 2 diabetes. We studied the Zucker fatty rat, as this is a model of insulin resistance, hyperglycemia, hyperlipidemia and obesity. This model, in certain respects, at least, typifies the characteristics of human subjects with type 2 diabetes. Our studies showed that upon induction of balloon injury in the carotid arteries of these rats, compared with lean, non-hyperglycemic control rats, an nearly two-fold increase in neointimal area after balloon injury resulted. This rat model therefore provided a means to dissect the contributory factors involved in diabetic complications.

In this context, the accumulation of late-stage glycoxidation adducts of proteins, termed AGEs (Advanced Glycoxidation Endproducts), in diabetic tissues occurs at an accelerated rate due to increased levels of glucose, superimposed oxidant stress, and a chronic inflammatory component evident in macrovascular atherosclerotic, and restenotic vascular lesions. AGEs modify long-lived molecules in the blood vessel wall considerably before symptomatic atherosclerosis occurs, and exert their cellular effects in large part via engagement of RAGE (Receptor for AGEs) (4-5). RAGE is the only well-characterized signal transduction receptor which, on binding AGE ligands, activates intracellular pathways leading to chronic cellular perturbation in cells of the atherosclerotic vessel wall, including endothelium, mononuclear phagocytes, lymphocytes and smooth muscle cells (6).

Furthermore, RAGE also serves as a receptor for a family of inflammatory mediators, S100/calgranulin polypeptides, such as EN-RAGE (7), which coexist with AGEs at the site of atherosclerotic lesions and provide another ligand to reinforce sustained cellular stimulation mediated by RAGE. As we speculated that these findings are relevant to aggressive restenosis accompanying angioplasty in patients with diabetes, reflecting an underlying accelerated atherosclerotic process due, probably in large part, to smooth muscle cell migration, matrix production and proliferation, we tested these concepts in a rat model of exaggerated neointimal expansion after balloon injury to the carotid artery.

In previous studies, we found that blockade of RAGE, using soluble (s) RAGE (the extracelluar ligand binding domain of the receptor), suppressed the development of accelerated atherosclerosis in apolipoprotein E null mice (8). It was thus logical to administer sRAGE to fatty Zucker rats and test the hypothesis that suppression of expanded neointimal formation might ensue.

Materials and Methods

Induction of carotid artery balloon injury. Carotid arterial injury was induced in Fatty Zucker rats with a 2 French Fogarty balloon catheter (Baxter Health Care Corp., Santa Ana, Calif.). Certain rats, as detailed below, received murine soluble RAGE, 0.5 mg, the day prior to surgery, and then once daily for a total of 6 more days (total treatment; 7 days). The remaining rats received murine serum albumin, 0.5 mg/day as control. Injections were given by intraperitoneal route, in sterile-endotoxin-free phosphate-buffed saline. All Zucker fatty rats were sacrificed on day 21 following carotid arterial injury.

Upon induction of anesthesia, a midline abdominal incision was made and an 18-gauge intravenous catheter was introduced to the aortic bifurcation and the distal abdominal aorta was exposed. The aorta was flushed with 50 ml of Ringer's lactate solution at 120 mm Hg followed by in vivo fixation with 200 ml of 5% Histochoice infused over five minutes at 120 mm Hg. Once the infusion was begun in all animals, they were sacrificed with an overdose of Pentothal through the tail vein.

After five minutes of perfusion fixation, the entire right and left carotid arteries were embedded in paraffin and sectioned at 5 mm sections from the proximal to the distal end. Histologic morphometric and immunohistochemical studies were done utilizing these day 21 paraffin-embedded sections.

Treatment. Thirteen Zucker fatty rats were randomly assigned to treatment with sRAGE (n=7) or murine serum albumin (MSA) (n=6).

Analysis of lesions. Slides obtained from paraffin-embedded sections were stained with hematoxylin and eosin (H&E) and elastic van Giessen stains. Morphometric analysis of the arterial segments was carried out by an observer blinded to the treatment groups. The investigator utilized a computerized digital microscopic telemetry algorithm (NIH Image 1.56). The cross-sectional areas of the lumen, intima, media and the visceral area as circumscribed the external elastic lamina were determined. Analysis was performed using sections stained with H&E under 40× microscopic magnification.

Results

The key index of an exaggerated response to arterial injury is the extent of neointimal formation. In fatty Zucker rats treated with sRAGE, there was a significant reduction in neointimal area compared with MSA-treated animals (0.8 mm$^2$ compared with 0.15 mm$^2$, respectively; p=0.001) (FIG. 1). Consistent with this observation, the neointimal to media ration for sRAGE-treated Zucker fatty rats was 0.83, compared to 1.43 mm$^2$ in rats treated with MSA; p=0.005 (FIG. 2).

Preliminary studies have been performed to determine the mechanism underlying the beneficial effects of sRAGE. Rats undergoing balloon injury were treated with sRAGE or MSA. Prior to sacrifice, rats were treated with multiple intraperitoneal injections of bromodeoxyrudine (BrdU). On day 5 after balloon injury, our preliminary studies have shown a reduction in smooth muscle proliferation and migration, as evidenced by the amount of BrdU positive cells staining in the media and intima in rats treated with sRAGE vs MSA (18% vs 25.4% Brdu-positive cells, respectively). We are now in the process of expanding the numbers of animals to be included in these mechanistic studies, and in testing the effects of sRAGE on various days after injury.

Discussion

One consequence of the endogenous development of accelerated atherosclerosis in subjects with diabetes is the need for revascularization in order to ensure adequate coronary flow and to minimize ischemic episodes. In such cases, one course of therapy includes the exogenous introduction of balloon catheter devices to disrupt intimal vascular lesions, thereby leading to revascularization and enhanced blood flow. In the case of subjects with diabetes, the response to percutaneous balloon catheter mediated revascularization is often untoward, with excessive formation of neointima, itself a risk for further ischemic episodes or infarction. Here we have shown the first time the blockade of RAGE, by administration of soluble RAGE, suppresses exaggerated neointimal expansion. These findings provide a novel means to prevent excessive restenosis in subjects with diabetes.

REFERENCES

1. Rosenman, Y., Sapoznikov, D., Mosseri, M., Gilon, D., Lotan, C., Nassar, H., Weiss, A. T., Hasin, Y., and Gotsman, M. S. Long-term angiographic follow-up of coronary balloon angioplasty in patients with diabetes mellitus: a clue to the explanation of the results of the BARI study (Balloon Angioplasty Revascularization Investigation). J. Am. Coll. Cardiol. 30:1420-1425, 1997.
2. Detre, K. M., Lomardero, M. S., Mori Brooks, M., Hardison, R. M., Holubkov, R., Sopko, G., Frye, R. L., and Chiatman, B. R. For the Bari investigators. The effect of previous coronary artery bypass surgery on the prognosis of patients with diabetes who have acute myocardial infarction. N. Engl. J. Med. 342:989-997, 2000.
3. Gu, K., Covie, C. C., and Harris, M. I. Diabetes and the Decline in heart disease mortality in United States Adults. JAMA 281:1291-1297, 1999.
4. Schmidt, A. M., Vianna, M., Gerlach, M., Breett, J., Ryan, J., Kao, J., Esposito, C., Hegarty, H., Hurley, W., Clauss, M., Wang, F., Pan, Y. C., Tsang, T. C., and Stern, D. Isolation and characterization of binding proteins for advanced glycosylation end products from lung tissue which are present on the endothelial cell surface. J. Biol. Chem. 267:14987-14997, 1992.
5. Neeper, M., Schmidt, A. M., Brett, J., Yan, S. D., Wang, F., Pan, Y. C., Elliston, K., Stern, D., and Shaw, A. Cloning and expression of RAGE: a cell surface receptor for advanced glycosylation end products of proteins. J. Biol. Chem. 267:14998-15004, 1992.
6. Lander, H. L., Tauras, J. M., Ogiste, J. S., Moss, R. A., and A. M. Schmidt. Activation of the Receptor for Advanced Glycation Endproducts triggers a MAP Kinase pathway regulated by oxidant stress. J. biol. Chem. 272:17810-17814, 1997.
7. Hoffman, M. A., Drury, S., Fu, C., Qu, W., Taguchi, A., Lu, Y., Avila, C., Kambham, N., Bierhaus, A., Nawroth, P., Neurath, M. F., Slattery, T., Beach, D., McClary, J., Nagashima, M., Morser, J., Stern, D., and Schmidt, A. M. RAGE mediates a novel proinflammatory axis: a central cell surface receptor for S100/calgranulin polypeptides. Cell 97:889-901, 1999.
8. Park, L., Raman, K. G., Lee, K. J., Yan, L., Ferran, L. J., Chow, W. S., Stern, D., and Schmidt, A. M. Suppression of accelerated diabetic atherosclerosis by soluble Receptor for AGE (sRAGE). Nature medicine 4:1025-1031, 1998.

What is claimed is:

1. A method for inhibiting neointimal formation in blood vessels in a subject, wherein the subject experienced blood vessel injury, comprising administering to the subject a soluble fragment of a receptor for advanced glycation endproducts polypeptide which fragment is coupled to an antibody in an amount effective to inhibit neointimal formation in the subject's blood vessels.

2. The method of claim 1, wherein the sequence of the receptor for advanced glycation endproduct is set forth in SEQ ID NO:1, 3, or 5.

3. The method of claim 1, wherein the subject is a non-human animal, a transgenic non-human animal or a human.

4. The method of claim 1, wherein the subject has undergone an angioplasty procedure or has undergone surgery to implant a stent in a blood vessel.

5. The method of claim 1, wherein the soluble fragment is administered to the subject by bolus injection, intraperitoneal injection, intravenous administration, subcutaneous administration, oral administration, topical application to the blood vessel, coating of a device to be placed within the subject, coating of an instrument used during a procedure upon the subject which results in a blood vessel injury or contacting the blood of the subject during extracorporeal circulation.

6. The method of claim 1, wherein the soluble fragment is administered to the subject by subcutaneous or intraperitoneal administration.

7. The method of claim 1, wherein the soluble fragment is administered to the subject at a rate from about 2 µg/kg/hr to about 100 µg/kg/hr.

8. The method of claim 1, wherein the soluble fragment of the receptor for advanced glycation endproducts polypeptide coupled to the antibody is coated onto a stent used during an angioplasty of the subject.

* * * * *

```
                             SEQUENCE LISTING

<160> NUMBER OF SEQ ID NOS: 6

<210> SEQ ID NO 1
<211> LENGTH: 416
<212> TYPE: PRT
<213> ORGANISM: Cow

<400> SEQUENCE: 1

Met Ala Ala Gly Ala Val Val Gly Ala Trp Met Leu Val Leu Ser Leu
1               5                   10                  15

Gly Gly Thr Val Thr Gly Asp Gln Asn Ile Thr Ala Arg Ile Gly Lys
            20                  25                  30

Pro Leu Val Leu Asn Cys Lys Gly Ala Pro Lys Lys Pro Pro Gln Gln
        35                  40                  45

Leu Glu Trp Lys Leu Asn Thr Gly Arg Thr Glu Ala Trp Lys Val Leu
    50                  55                  60

Ser Pro Gln Gly Asp Pro Trp Asp Ser Val Ala Arg Val Leu Pro Asn
65                  70                  75                  80

Gly Ser Leu Leu Leu Pro Ala Val Gly Ile Gln Asp Glu Gly Thr Phe
                85                  90                  95

Arg Cys Arg Ala Thr Ser Arg Ser Gly Lys Glu Thr Lys Ser Asn Tyr
            100                 105                 110

Arg Val Arg Val Tyr Gln Ile Pro Gly Lys Pro Glu Ile Val Asp Pro
        115                 120                 125

Ala Ser Glu Leu Met Ala Gly Val Pro Asn Lys Val Gly Thr Cys Val
130                 135                 140

Ser Glu Gly Gly Tyr Pro Ala Gly Thr Leu Asn Trp Leu Leu Asp Gly
145                 150                 155                 160

Lys Thr Leu Ile Pro Asp Gly Lys Gly Val Ser Val Lys Glu Glu Thr
            165                 170                 175

Lys Arg His Pro Lys Thr Gly Leu Phe Thr Leu His Ser Glu Leu Met
        180                 185                 190

Val Thr Pro Ala Arg Gly Gly Ala Leu His Pro Thr Phe Ser Cys Ser
    195                 200                 205

Phe Thr Pro Gly Leu Pro Arg Arg Arg Ala Leu His Thr Ala Pro Ile
210                 215                 220

Gln Leu Arg Val Trp Ser Glu His Arg Gly Gly Glu Gly Pro Asn Val
225                 230                 235                 240

Asp Ala Val Pro Leu Lys Glu Val Gln Leu Val Val Glu Pro Glu Gly
            245                 250                 255

Gly Ala Val Ala Pro Gly Gly Thr Val Thr Leu Thr Cys Glu Ala Pro
        260                 265                 270

Ala Gln Pro Pro Pro Gln Ile His Trp Ile Lys Asp Gly Arg Pro Leu
    275                 280                 285

Pro Leu Pro Pro Gly Pro Met Leu Leu Leu Pro Glu Val Gly Pro Glu
290                 295                 300

Asp Gln Gly Thr Tyr Ser Cys Val Ala Thr His Pro Ser His Gly Pro
305                 310                 315                 320

Gln Glu Ser Arg Ala Val Ser Val Thr Ile Ile Glu Thr Gly Glu Glu
            325                 330                 335

Gly Thr Thr Ala Gly Ser Val Glu Gly Pro Gly Leu Glu Thr Leu Ala
        340                 345                 350

Leu Thr Leu Gly Ile Leu Gly Gly Leu Gly Thr Val Ala Leu Leu Ile
    355                 360                 365
```

Gly Val Ile Val Trp His Arg Arg Gln Arg Lys Gly Gln Glu Arg
    370             375             380

Lys Val Pro Glu Asn Gln Glu Glu Glu Glu Arg Ala Glu Leu
385             390             395             400

Asn Gln Pro Glu Glu Pro Glu Ala Ala Glu Ser Ser Thr Gly Gly Pro
            405             410             415

<210> SEQ ID NO 2
<211> LENGTH: 1426
<212> TYPE: DNA
<213> ORGANISM: Cow

<400> SEQUENCE: 2

```
cggagaagga tggcagcagg ggcagtggtc ggagcctgga tgctagtcct cagtctgggg      60
gggacagtca cggggggacca aaacatcaca gcccggatcg ggaagccact ggtgctgaac    120
tgcaagggag cccccaagaa accaccccag cagctggaat ggaaactgaa cacaggccgg    180
acagaagctt ggaaagtcct gtctccccag ggagacccct gggatagcgt ggctcgggtc    240
ctccccaacg gctccctcct cctgccggct gttgggatcc aggatgaggg gactttccgg    300
tgccgggcaa cgagccggag cggaaaggag accaagtcta actaccgagt ccgagtctat    360
cagattcctg ggaagccaga aattgttgat cctgcctctg aactcatggc tggtgtcccc    420
aataaggtgg ggacatgtgt gtccgagggg ggctaccctg cagggactct taactggctc    480
ttggatggga aaactctgat tcctgatggc aaaggagtgt cagtgaagga agagaccaag    540
agacacccaa agacagggct tttcacgctc cattcggagc tgatggtgac cccagctcgg    600
ggaggagctc tccaccccac cttctcctgt agcttcaccc ctggccttcc ccggcgccga    660
gccctgcaca cggcccccat ccagctcagg gtctggagtg agcaccgagg tggggagggc    720
cccaacgtgg acgctgtgcc actgaaggaa gtccagttgg tggtagagcc agaaggggga    780
gcagtagctc ctggtggtac tgtgaccttg acctgtgaag cccccgccca gccccacct    840
caaatccact ggatcaagga tggcaggccc ctgccccttc ccctggccc catgctgctc    900
ctcccagagg tagggcctga ggaccaggga acctacagtt gtgtggccac ccatcccagc    960
catgggcccc aggagagccg tgctgtcagc gtcacgatca tcgaaacagg cgaggagggg   1020
acgactgcag gctctgtgga agggccgggg ctggaacccc tagccctgac cctggggatc   1080
ctggaggcc tgggacagt cgccctgctc attggggtca tcgtgtggca tcgaaggcgg   1140
caacgcaaag acaggagag aaggtcccg gaaaaccagg aggaggaaga ggaggagaga   1200
gcggaactga ccagccaga ggagcccgag gcggcagaga gcagcacagg agggccttga   1260
ggagcccacg gccagaccc gatccatcag cccttttctt ttcccacact ctgttctggc   1320
cccagaccag ttctcctctg tataatctcc agcccacatc tcccaaactt tcttccacaa   1380
ccagagcctc ccacaaaaag tgatgagtaa acacctgcca cattta                  1426
```

<210> SEQ ID NO 3
<211> LENGTH: 404
<212> TYPE: PRT
<213> ORGANISM: Human

<400> SEQUENCE: 3

Gly Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

```
Pro Leu Val Leu Lys Cys Lys Gly Ala Pro Lys Lys Pro Gln Arg
     35                  40                  45
Leu Glu Trp Lys Leu Asn Thr Gly Arg Thr Glu Ala Trp Lys Val Leu
 50                  55                  60
Ser Pro Gln Gly Gly Pro Trp Asp Ser Val Ala Arg Val Leu Pro
 65                  70                  75                  80
Asn Gly Ser Leu Phe Leu Pro Ala Val Gly Ile Gln Asp Glu Gly Ile
                 85                  90                  95
Phe Arg Cys Arg Ala Met Asn Arg Asn Gly Lys Glu Thr Lys Ser Asn
                100                 105                 110
Tyr Arg Val Arg Val Tyr Gln Ile Pro Gly Lys Pro Glu Ile Val Asp
                115                 120                 125
Ser Ala Ser Glu Leu Thr Ala Gly Val Pro Asn Lys Val Gly Thr Cys
130                 135                 140
Val Ser Glu Gly Ser Tyr Pro Ala Gly Thr Leu Ser Trp His Leu Asp
145                 150                 155                 160
Gly Lys Pro Leu Val Pro Asn Glu Lys Gly Val Ser Val Lys Glu Gln
                165                 170                 175
Thr Arg Arg His Pro Glu Thr Gly Leu Phe Thr Leu Gln Ser Glu Leu
                180                 185                 190
Met Val Thr Pro Ala Arg Gly Gly Asp Pro Arg Pro Thr Phe Ser Cys
                195                 200                 205
Ser Phe Ser Pro Gly Leu Pro Arg His Arg Ala Leu Arg Thr Ala Pro
210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
                260                 265                 270
Lys Asp Gly Val Pro Leu Pro Leu Pro Pro Ser Pro Val Leu Ile Leu
                275                 280                 285
Pro Glu Ile Gly Pro Gln Asp Gln Gly Thr Tyr Ser Cys Val Ala Thr
290                 295                 300
His Ser Ser His Gly Pro Gln Glu Ser Arg Ala Val Ser Ile Ser Ile
305                 310                 315                 320
Ile Glu Pro Gly Glu Glu Gly Pro Thr Ala Gly Ser Val Gly Gly Ser
                325                 330                 335
Gly Leu Gly Thr Leu Ala Leu Ala Leu Gly Ile Leu Gly Gly Leu Gly
                340                 345                 350
Thr Ala Ala Leu Leu Ile Gly Val Ile Leu Trp Gln Arg Arg Gln Arg
                355                 360                 365
Arg Gly Glu Glu Arg Lys Ala Pro Glu Asn Gln Glu Glu Glu Glu Glu
                370                 375                 380
Arg Ala Glu Leu Asn Gln Ser Glu Glu Pro Glu Ala Gly Glu Ser Ser
385                 390                 395                 400
Thr Gly Gly Pro

<210> SEQ ID NO 4
<211> LENGTH: 1391
<212> TYPE: DNA
<213> ORGANISM: Human

<400> SEQUENCE: 4
ggggcagccg gaacagcagt tggagcctgg gtgctggtcc tcagtctgtg gggggcagta        60
```

```
gtaggtgctc aaaacatcac agcccggatt ggcgagccac tggtgctgaa gtgtaagggg      120
gcccccaaga aaccacccca gcggctggaa tggaaactga acacaggccg acagaagct       180 tggaaggtcc tgtctcccca gggaggaggc ccctgggaca gtgtggctcg tgtccttccc      240
aacggctccc tcttccttcc ggctgtcggg atccaggatg aggggatttt ccggtgcagg      300
gcaatgaaca ggaatggaaa ggagaccaag tccaactacc gagtccgtgt ctaccagatt      360
cctgggaagc cagaaattgt agattctgcc tctgaactca cggctggtgt tcccaataag      420
gtggggacat gtgtgtcaga gggaagctac cctgcaggga ctcttagctg gcacttggat      480
gggaagcccc tggtgcctaa tgagaaggga gtatctgtga aggaacagac caggagacac      540
cctgagacag ggctcttcac actgcagtcg gagctaatgg tgaccccagc ccggggagga      600 gatcccgtc ccaccttctc ctgtagcttc agcccaggcc ttccccgaca ccgggccttg       660
cgcacagccc ccatccagcc ccgtgtctgg gagcctgtgc ctctggagga ggtccaattg      720
gtggtggagc cagaaggtgg agcagtagct cctggtggaa ccgtaaccct gacctgtgaa      780
gtccctgccc agccctctcc tcaaatccac tggatgaagg atggtgtgcc cttgccctt      840 cccccagcc ctgtgctgat cctccctgag atagggcctc aggaccaggg aacctacagc       900
tgtgtggcca cccattccag ccacgggccc caggaaagcc gtgctgtcag catcagcatc      960
atcgaaccag gcgaggaggg gccaactgca ggctctgtgg gaggatcagg gctgggaact     1020
ctagccctgg ccctggggat cctgggaggc ctggggacag ccgccctgct cattggggtc     1080
atcttgtggc aaaggcggca acgccgagga gagagagga aggccccaga aaaccaggag      1140
gaagaggagg agcgtgcaga actgaatcag tcggaggaac ctgaggcagg cgagagtagt     1200
actggagggc cttgaggggc ccacagacag atcccatcca tcagctccct tttctttttc     1260
ccttgaactg ttctggcctc agaccaactc tctcctgtat aatctctctc ctgtataacc     1320
ccaccttgcc aagctttctt ctacaaccag agcccccac aatgatgatt aaacacctga     1380
cacatcttgc a                                                         1391
```

<210> SEQ ID NO 5
<211> LENGTH: 403
<212> TYPE: PRT
<213> ORGANISM: Mouse

<400> SEQUENCE: 5

```
Met Pro Ala Gly Thr Ala Ala Arg Ala Trp Val Leu Val Leu Ala Leu
1               5                   10                  15

Trp Gly Ala Val Ala Gly Gly Gln Asn Ile Thr Ala Arg Ile Gly Glu
            20                  25                  30

Pro Leu Val Leu Ser Cys Lys Gly Ala Pro Lys Lys Pro Pro Gln Gln
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Gln Ile Leu Pro Asn
65                  70                  75                  80

Gly Ser Leu Leu Leu Pro Ala Thr Gly Ile Val Asp Glu Gly Thr Phe
                85                  90                  95

Arg Cys Arg Ala Thr Asn Arg Arg Gly Lys Glu Val Lys Ser Asn Tyr
            100                 105                 110

Arg Val Arg Val Tyr Gln Ile Pro Gly Lys Pro Glu Ile Val Asp Pro
        115                 120                 125

Ala Ser Glu Leu Thr Ala Ser Val Pro Asn Lys Val Gly Thr Cys Val
```

```
            130                 135                 140
Ser Glu Gly Ser Tyr Pro Ala Gly Thr Leu Ser Trp His Leu Asp Gly
145                 150                 155                 160

Lys Leu Leu Ile Pro Asp Gly Lys Glu Thr Leu Val Lys Glu Thr
            165                 170                 175

Arg Arg His Pro Glu Thr Gly Leu Phe Thr Leu Arg Ser Glu Leu Thr
            180                 185                 190

Val Ile Pro Thr Gln Gly Gly Thr His Pro Thr Phe Ser Cys Ser
            195                 200                 205

Phe Ser Leu Gly Leu Pro Arg Arg Arg Pro Leu Asn Thr Ala Pro Ile
210                 215                 220

Gln Leu Arg Val Arg Glu Pro Gly Pro Pro Glu Gly Ile Gln Leu Leu
225                 230                 235                 240

Val Glu Pro Glu Gly Gly Ile Val Ala Pro Gly Gly Thr Val Thr Leu
            245                 250                 255

Thr Cys Ala Ile Ser Ala Gln Pro Pro Pro Gln Val His Trp Ile Lys
            260                 265                 270

Asp Gly Ala Pro Leu Pro Leu Ala Pro Ser Pro Val Leu Leu Leu Pro
            275                 280                 285

Glu Val Gly His Ala Asp Glu Gly Thr Tyr Ser Cys Val Ala Thr His
            290                 295                 300

Pro Ser His Gly Pro Gln Glu Ser Pro Pro Val Ser Ile Arg Val Thr
305                 310                 315                 320

Glu Thr Gly Asp Glu Gly Pro Ala Glu Gly Ser Val Gly Glu Ser Gly
                        325                 330                 335

Leu Gly Thr Leu Ala Leu Ala Leu Gly Ile Leu Gly Gly Leu Gly Val
            340                 345                 350

Val Ala Leu Leu Val Gly Ala Ile Leu Trp Arg Lys Arg Gln Pro Arg
            355                 360                 365

Arg Glu Glu Arg Lys Ala Pro Glu Ser Gln Glu Asp Glu Glu Glu Arg
            370                 375                 380

Ala Glu Leu Asn Gln Ser Glu Glu Ala Glu Met Pro Glu Asn Gly Ala
385                 390                 395                 400

Gly Gly Pro

<210> SEQ ID NO 6
<211> LENGTH: 1348
<212> TYPE: DNA
<213> ORGANISM: Mouse

<400> SEQUENCE: 6
gcaccatgcc agcggggaca gcagctagag cctgggtgct ggttcttgct ctatgggag     60 ctgtagctgg tggtcagaac atcacagccc ggattggaga gccacttgtg ctaagctgta   120 aggggggccccc taagaagccg ccccagcagc tagaatggaa actgaacaca ggaagaactg  180
aagcttggaa ggtcctctct ccccagggag gcccctggga cagcgtggct caaatcctcc   240
ccaatggttc cctcctcctt ccagccactg gaattgtcga tgaggggacg ttccggtgtc   300
gggcaactaa caggcgaggg aaggaggtca agtccaacta ccgagtccga gtctaccaga   360
ttcctgggaa gccagaaatt gtggatcctg cctctgaact cacagccagt gtccctaata   420
aggtggggac atgtgtgtct gagggaagct accctgcagg gacccttagc tggcacttag   480
atgggaaact tctgattccc gatggcaaag aaacactcgt gaaggaagag accaggagac   540
accctgagac gggactcttt acactgcggt cagagctgac agtgatcccc acccaaggag   600
```

```
gaaccaccca tcctaccttc tcctgcagtt tcagcctggg ccttccccgg cgcagacccc    660
tgaacacagc ccctatccaa ctccgagtca gggagcctgg gcctccagag ggcattcagc    720
tgttggttga gcctgaaggt ggaatagtcg ctcctggtgg gactgtgacc ttgacctgtg    780
ccatctctgc ccagccccct cctcaggtcc actggataaa ggatggtgca cccttgcccc    840
tggctcccag ccctgtgctg ctcctccctg aggtggggca cgcggatgag ggcacctata    900
gctgcgtggc cacccaccct agccacggac ctcaggaaag ccctcctgtc agcatcaggg    960
tcacagaaac cggcgatgag gggccagctg aaggctctgt gggtgagtct gggctgggta   1020
cgctagccct ggccttgggg atcctgggag gcctgggagt agtagccctg ctcgtcgggg   1080
ctatcctgtg gcgaaaacga caacccaggc gtgaggagag gaaggccccg gaaagccagg   1140
aggatgagga ggaacgtgca gagctgaatc agtcagagga agcggagatg ccagagaatg   1200
gtgccggggg accgtaagag cacccagatc gagcctgtgt gatggcccta gagcagctcc   1260
cccacattcc atcccaattc ctccttgagg cacttccttc tccaaccaga gcccacatga   1320
tccatgctga gtaaacattt gatacggc                                      1348
```